(12) United States Patent
Dye

(10) Patent No.: US 7,988,695 B2
(45) Date of Patent: Aug. 2, 2011

(54) ARTICULATED DELIVERY INSTRUMENT

(75) Inventor: Justin Dye, Mansfield, MA (US)

(73) Assignee: Theken Spine, LLC, Akron, OH (US)

( * ) Notice: Subject to any disclaimer, the term of this patent is extended or adjusted under 35 U.S.C. 154(b) by 1126 days.

(21) Appl. No.: 11/614,540

(22) Filed: Dec. 21, 2006

(65) Prior Publication Data
US 2007/0142843 A1 Jun. 21, 2007

Related U.S. Application Data

(60) Provisional application No. 60/752,544, filed on Dec. 21, 2005.

(51) Int. Cl.
*A61B 17/70* (2006.01)
(52) U.S. Cl. ........ 606/86 A; 606/99
(58) Field of Classification Search ........ 606/86 A, 606/90, 99
See application file for complete search history.

(56) References Cited

U.S. PATENT DOCUMENTS

| | | | |
|---|---|---|---|
| 3,136,040 A | 6/1964 | Bauer | |
| 3,486,505 A * | 12/1969 | Morrison | 606/90 |
| 4,501,269 A | 2/1985 | Bagby | |
| 4,714,469 A | 12/1987 | Kenna | |
| 4,863,477 A | 9/1989 | Monson | |
| 4,878,915 A | 11/1989 | Brantigan | |
| 4,997,432 A | 3/1991 | Keller | |
| 5,059,193 A | 10/1991 | Kuslich | |
| 5,171,278 A | 12/1992 | Pisharodi | |
| 5,390,683 A | 2/1995 | Pisharodi | |
| 5,484,437 A | 1/1996 | Michelson | |
| 5,554,191 A | 9/1996 | Lahille et al. | |
| 5,562,736 A | 10/1996 | Ray et al. | |
| 5,653,762 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,449 A | 12/1997 | McKay | |
| 5,713,899 A | 2/1998 | Marnay et al. | |
| 5,716,415 A | 2/1998 | Steffee | |
| 5,741,253 A | 4/1998 | Michelson | |
| 5,749,916 A | 5/1998 | Richelsoph | |
| 5,776,199 A | 7/1998 | Michelson | |
| 5,782,830 A | 7/1998 | Farris | |
| 5,797,909 A | 8/1998 | Michelson | |
| 5,800,550 A | 9/1998 | Sertich | |
| 5,860,973 A | 1/1999 | Michelson | |

(Continued)

FOREIGN PATENT DOCUMENTS

| | | |
|---|---|---|
| WO | WO-9526164 | 10/1995 |
| WO | WO 98/01091 A1 | 1/1998 |
| WO | WO-9909913 | 3/1999 |
| WO | WO-0024343 | 5/2000 |
| WO | WO-0025687 | 5/2000 |
| WO | WO-0066045 | 11/2000 |
| WO | WO-0128465 | 4/2001 |
| WO | WO-0128468 | 4/2001 |
| WO | WO-0217823 | 3/2002 |
| WO | WO-02058594 | 8/2002 |
| WO | WO-2005009299 | 2/2005 |

*Primary Examiner* — Thomas C Barrett
*Assistant Examiner* — Christine L Nelson
(74) *Attorney, Agent, or Firm* — Middleton Reutlinger; Robert H. Eichenberger; Chad D. Bruggeman

(57) ABSTRACT

An articulated delivery instrument for the proper positioning and placements of inserts, for example, an insert such as a lumbar interbody fusion device ("LIF"). The instrument may comprise a body and a first member slidingly coupled to the body. A rotating member for releasably retaining an insert may be pivotally coupled to a distal end of the body and the first member. A first actuator may function to translate the first member relative to the body. Translation of the first member relative to the body may rotate the rotating member relative to the instrument. A second actuator may function to transition the rotating member between release and retention of the insert.

14 Claims, 3 Drawing Sheets

U.S. PATENT DOCUMENTS

| | | |
|---|---|---|
| 5,885,299 A | 3/1999 | Winslow et al. |
| 5,888,228 A | 3/1999 | Knothe et al. |
| 6,033,405 A | 3/2000 | Winslow et al. |
| 6,039,761 A | 3/2000 | Li et al. |
| 6,039,762 A | 3/2000 | McKay |
| 6,059,790 A | 5/2000 | Sand et al. |
| 6,074,423 A | 6/2000 | Lawson |
| 6,080,155 A | 6/2000 | Michelson |
| 6,093,207 A | 7/2000 | Pisharodi |
| 6,096,038 A | 8/2000 | Michelson |
| 6,123,705 A | 9/2000 | Michelson |
| 6,143,032 A | 11/2000 | Schafer et al. |
| 6,174,334 B1 | 1/2001 | Suddaby |
| 6,183,517 B1 | 2/2001 | Suddaby |
| 6,206,923 B1 | 3/2001 | Boyd et al. |
| 6,214,050 B1 | 4/2001 | Huene |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,319,257 B1 | 11/2001 | Carignan et al. |
| 6,328,738 B1 | 12/2001 | Suddaby |
| 6,368,325 B1 | 4/2002 | McKinley et al. |
| 6,387,130 B1 | 5/2002 | Stone et al. |
| 6,402,750 B1 | 6/2002 | Atkinson et al. |
| 6,419,704 B1 | 7/2002 | Ferree |
| 6,436,098 B1 | 8/2002 | Michelson |
| 6,440,142 B1 | 8/2002 | Ralph et al. |
| 6,447,547 B1 | 9/2002 | Michelson |
| 6,451,019 B1 | 9/2002 | Zucherman et al. |
| 6,478,823 B1 | 11/2002 | Michelson |
| 6,488,710 B2 | 12/2002 | Besselink |
| 6,491,695 B1 | 12/2002 | Roggenbuck |
| 6,491,724 B1 | 12/2002 | Ferree |
| 6,511,484 B2 | 1/2003 | Torode et al. |
| 6,520,967 B1 | 2/2003 | Cauthen |
| 6,533,791 B1 | 3/2003 | Betz et al. |
| 6,575,978 B2 | 6/2003 | Peterson et al. |
| 6,595,995 B2 | 7/2003 | Zdeblick et al. |
| 6,599,291 B1 | 7/2003 | Foley et al. |
| 6,599,294 B2 | 7/2003 | Fuss et al. |
| 6,610,089 B1 | 8/2003 | Liu et al. |
| 6,613,089 B1 | 9/2003 | Estes et al. |
| 6,620,196 B1 | 9/2003 | Trieu |
| 6,635,060 B2 | 10/2003 | Hanson et al. |
| 6,652,533 B2 | 11/2003 | O'Neil |
| 6,666,866 B2 | 12/2003 | Martz et al. |
| 6,666,889 B1 | 12/2003 | Commarmond |
| 6,699,288 B2 | 3/2004 | Moret |
| 6,712,819 B2 | 3/2004 | Zucherman et al. |
| 6,716,247 B2 | 4/2004 | Michelson |
| 6,719,794 B2 | 4/2004 | Gerber et al. |
| 6,733,504 B2 | 5/2004 | Lin et al. |
| 6,733,534 B2 | 5/2004 | Sherman |
| 6,743,255 B2 | 6/2004 | Ferree |
| 6,746,454 B2 | 6/2004 | Winterbottom et al. |
| 6,746,484 B1 | 6/2004 | Liu et al. |
| 6,755,837 B2 | 6/2004 | Ebner |
| 6,764,491 B2 | 7/2004 | Frey et al. |
| 6,767,366 B2 | 7/2004 | Lee et al. |
| 6,793,679 B2 | 9/2004 | Michelson |
| 6,805,695 B2 | 10/2004 | Keith et al. |
| 6,814,737 B2 | 11/2004 | Cauthen |
| 6,830,570 B1 | 12/2004 | Frey et al. |
| 6,830,574 B2 | 12/2004 | Heckele et al. |
| 6,837,905 B1 | 1/2005 | Lieberman |
| 6,875,213 B2 | 4/2005 | Michelson |
| 6,893,464 B2 | 5/2005 | Kiester |
| 6,923,811 B1 | 8/2005 | Carl et al. |
| 6,923,813 B2 | 8/2005 | Phillips et al. |
| 6,929,647 B2 | 8/2005 | Cohen |
| 6,939,318 B2 | 9/2005 | Stenzel |
| 6,974,480 B2 | 12/2005 | Messerli et al. |
| 6,986,772 B2 | 1/2006 | Michelson |
| 7,063,725 B2 | 6/2006 | Foley |
| 7,087,055 B2 | 8/2006 | Lim et al. |
| 7,115,132 B2 | 10/2006 | Errico et al. |
| 7,147,641 B2 | 12/2006 | Chen |
| 7,235,081 B2 | 6/2007 | Errico et al. |
| 7,235,082 B2 | 6/2007 | Bartish et al. |
| 7,244,258 B2 | 7/2007 | Burkus et al. |
| 7,500,991 B2 | 3/2009 | Bartish et al. |
| 7,559,930 B2 | 7/2009 | Allard et al. |
| 7,575,580 B2 * | 8/2009 | Lim et al. .................. 606/99 |
| 7,608,080 B2 * | 10/2009 | Shipp et al. .................. 606/99 |
| 7,648,506 B2 | 1/2010 | McCord et al. |
| 2001/0034553 A1 | 10/2001 | Michelson |
| 2002/0022856 A1 | 2/2002 | Johnson et al. |
| 2002/0026244 A1 | 2/2002 | Trieu |
| 2002/0065558 A1 | 5/2002 | Varga et al. |
| 2002/0065560 A1 | 5/2002 | Varga et al. |
| 2002/0077700 A1 | 6/2002 | Varga et al. |
| 2002/0091390 A1 | 7/2002 | Michelson |
| 2002/0116006 A1 | 8/2002 | Cohen |
| 2002/0161443 A1 | 10/2002 | Michelson |
| 2002/0165550 A1 | 11/2002 | Frey et al. |
| 2002/0173851 A1 | 11/2002 | McKay |
| 2003/0014118 A1 | 1/2003 | Lambrecht et al. |
| 2003/0065394 A1 | 4/2003 | Michelson |
| 2003/0074075 A1 | 4/2003 | Thomas et al. |
| 2003/0083747 A1 | 5/2003 | Winterbottom et al. |
| 2003/0093155 A1 | 5/2003 | Lambrecht et al. |
| 2003/0105527 A1 | 6/2003 | Bresina et al. |
| 2003/0135275 A1 | 7/2003 | Garcia et al. |
| 2003/0135279 A1 | 7/2003 | Michelson |
| 2003/0139816 A1 | 7/2003 | Michelson |
| 2003/0149482 A1 | 8/2003 | Michelson |
| 2003/0176926 A1 | 9/2003 | Boehm et al. |
| 2003/0199983 A1 | 10/2003 | Michelson |
| 2003/0208203 A1 | 11/2003 | Lim et al. |
| 2004/0002719 A1 * | 1/2004 | Oz et al. .................. 606/142 |
| 2004/0030392 A1 | 2/2004 | Lambrecht et al. |
| 2004/0039392 A1 | 2/2004 | Trieu |
| 2004/0044412 A1 | 3/2004 | Lambrecht |
| 2004/0117020 A1 | 6/2004 | Frey et al. |
| 2004/0127990 A1 | 7/2004 | Bartish et al. |
| 2004/0133280 A1 | 7/2004 | Trieu |
| 2004/0153065 A1 * | 8/2004 | Lim .................. 606/53 |
| 2004/0193271 A1 | 9/2004 | Fraser et al. |
| 2004/0210315 A1 | 10/2004 | Li et al. |
| 2004/0225361 A1 | 11/2004 | Glenn et al. |
| 2005/0027360 A1 | 2/2005 | Webb et al. |
| 2005/0033305 A1 * | 2/2005 | Schultz .................. 606/99 |
| 2005/0038431 A1 | 2/2005 | Bartish et al. |
| 2005/0038513 A1 | 2/2005 | Michelson |
| 2005/0070900 A1 | 3/2005 | Serhan et al. |
| 2005/0080422 A1 | 4/2005 | Otte et al. |
| 2005/0090824 A1 | 4/2005 | Shluzas et al. |
| 2005/0096745 A1 | 5/2005 | Andre et al. |
| 2005/0113838 A1 | 5/2005 | Phillips et al. |
| 2005/0119747 A1 | 6/2005 | Fabris et al. |
| 2005/0131419 A1 | 6/2005 | McCord et al. |
| 2005/0131420 A1 | 6/2005 | Techiera et al. |
| 2005/0143749 A1 * | 6/2005 | Zalenski et al. .................. 606/99 |
| 2005/0143822 A1 | 6/2005 | Paul |
| 2005/0143827 A1 | 6/2005 | Globerman et al. |
| 2005/0149195 A1 | 7/2005 | Boyd et al. |
| 2005/0149197 A1 | 7/2005 | Cauthen |
| 2005/0159817 A1 | 7/2005 | Ferree |
| 2005/0171609 A1 | 8/2005 | Humphreys et al. |
| 2005/0187625 A1 | 8/2005 | Wolek et al. |
| 2005/0187629 A1 | 8/2005 | Michelson |
| 2005/0261681 A9 | 11/2005 | Branch et al. |
| 2005/0278027 A1 | 12/2005 | Hyde et al. |
| 2006/0004376 A1 | 1/2006 | Schipp et al. |
| 2006/0004456 A1 | 1/2006 | McKay |
| 2006/0129244 A1 | 6/2006 | Ensign |
| 2006/0178673 A1 | 8/2006 | Curran |
| 2006/0200164 A1 | 9/2006 | Michelson |
| 2006/0229627 A1 | 10/2006 | Hunt et al. |
| 2006/0235426 A1 | 10/2006 | Lim et al. |
| 2006/0241641 A1 * | 10/2006 | Albans et al. .................. 606/90 |
| 2006/0241761 A1 | 10/2006 | Gately |
| 2007/0010826 A1 | 1/2007 | Rhoda et al. |
| 2007/0067035 A1 | 3/2007 | Falahee |
| 2007/0123985 A1 | 5/2007 | Errico et al. |
| 2007/0225726 A1 | 9/2007 | Dye et al. |

| | | | | | | |
|---|---|---|---|---|---|---|
| 2007/0225808 A1 | 9/2007 | Warnick | | 2008/0125865 A1 | 5/2008 | Abdelgany |
| 2007/0260314 A1 | 11/2007 | Biyani | | 2008/0140205 A1* | 6/2008 | Richelsoph ............... 623/17.16 |
| 2007/0276406 A1 | 11/2007 | Mahoney et al. | | 2009/0276049 A1 | 11/2009 | Weiland |
| 2008/0009880 A1 | 1/2008 | Warnick et al. | | | | |
| 2008/0077153 A1 | 3/2008 | Pernsteiner et al. | | | | |

* cited by examiner

ARTICULATED DELIVERY INSTRUMENT

CROSS-REFERENCE TO RELATED APPLICATIONS

This application relates to, and claims the benefit of the filing date of, U.S. provisional patent application Ser. No. 60/752,544 entitled "RETICULATED DELIVERY INSTRUMENT" filed Dec. 21, 2005, the entire contents of which are incorporated herein by reference for all purposes.

BACKGROUND OF THE INVENTION

1. Field of the Invention

This disclosure relates to systems and methods for stabilization of human spines, and, more particularly, to instruments for inserting spinal implants for lumbar interbody fusion devices.

2. Description of the Related Art

The human spine is a complex structure designed to achieve a myriad of tasks, many of them of a complex kinematic nature. The spinal vertebrae allow the spine to flex in three axes of movement relative to the portion of the spine in motion. These axes include the horizontal (bending either forward/anterior or aft/posterior), roll (lateral bending to either left or right side) and rotation (twisting of the shoulders relative to the pelvis).

The intervertebral spacing (between neighboring vertebrae) in a healthy spine is maintained by a compressible and somewhat elastic disc. The disc serves to allow the spine to move about the various axes of rotation and through the various arcs and movements required for normal mobility. The elasticity of the disc maintains spacing between the vertebrae, allowing room or clearance for compression of neighboring vertebrae, during flexion and lateral bending of the spine. In addition, the disc allows relative rotation about the vertical axis of neighboring vertebrae, allowing the twisting of the shoulders relative to the hips and pelvis. Clearance between neighboring vertebrae maintained by a healthy disc is also important to allow nerves from the spinal chord to extend out of the spine, between neighboring vertebrae, without being squeezed or impinged by the vertebrae.

In situations (based upon injury or otherwise) where a disc is not functioning properly, the inter-vertebral disc tends to compress, and in doing so pressure is exerted on nerves extending from the spinal cord by this reduced inter-vertebral spacing. Various other types of nerve problems may be experienced in the spine, such as exiting nerve root compression in neural foramen, passing nerve root compression, and enervated annulus (where nerves grow into a cracked/compromised annulus, causing pain every time the disc/annulus is compressed), as examples. Many medical procedures have been devised to alleviate such nerve compression and the pain that results from nerve pressure. Many of these procedures revolve around attempts to prevent the vertebrae from moving too close to each other by surgically removing an improperly functioning disc and replacing it with a lumbar interbody fusion device ("LIF"). Although prior interbody devices, including LIF cage devices, can be effective at improving patient condition, the vertebrae of the spine, body organs, the spinal cord, other nerves, and other adjacent bodily structures make it difficult to obtain surgical access to the location between the vertebrae where the LIF cage is to be installed.

Generally speaking, using a less invasive surgical technique for a spinal surgical procedure will minimize trauma to the surrounding bone, tissues and muscle and improve patient condition after the surgery. However, the size of the LIF cage itself often dictates a relatively large size for the required surgical opening. Accordingly, it would be desirable to reduce the size of the LIF cage to minimize the size for the required surgical opening for installation of the LIF cage, while maintaining high strength, durability and reliability of the LIF cage device. Furthermore, it would also be desirable to design instruments for delivering these types of spinal implants. Instruments that can minimize trauma to the patient and can deliver these spinal implants accurately and precisely will be desirable.

SUMMARY OF THE INVENTION

An embodiment of the present invention provides an instrument for delivering an insert. The instrument may comprise a body, a first member translatingly coupled to the body, and a rotating member pivotally connected to a distal end of the body and the first member. The rotating member may be configured to releasably retain the insert. The instrument may further comprise a first actuator coupled to the body and the first member. The first actuator may be configured to translate the first member with respect to the body. Additionally, the instrument may comprise a second actuator coupled to the rotating member. The second actuator may be configured to transition the rotating member between release and retention of the insert.

BRIEF DESCRIPTION OF THE DRAWINGS

For a more complete understanding of the present invention and the advantages thereof, reference is now made to the following Detailed Description taken in conjunction with the accompanying drawings, in which.

DETAILED DESCRIPTION

The entire contents of Provisional Patent Application Ser. No. 60/752,544 entitled "RETICULATED DELIVERY INSTRUMENT" filed Dec. 21, 2005, are incorporated herein by reference for all purposes. In the following discussion, numerous specific details are set forth to provide a thorough understanding of the present invention. However, those skilled in the art will appreciate that the present invention may be practiced without such specific details.

Figure 1A:
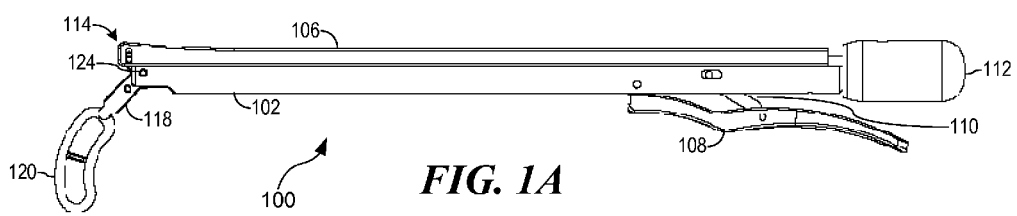
FIG. 1A is a sagittal view of an embodiment of a delivery instrument designed to insert a LIF cage into the intervertebral space.
Figure 1B:
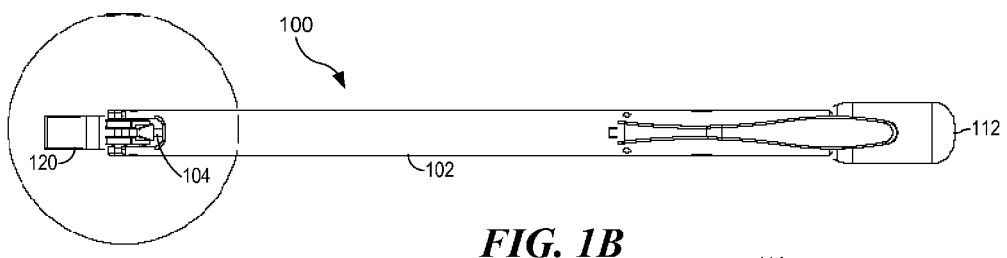
FIG. 1B is a bottom view of an embodiment of the delivery instrument of FIG. 1A.
Figure 1C:
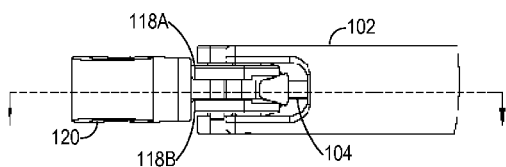
FIG. 1C is a detail view of an articulated joint of the delivery instrument shown in FIG. 1B.

FIG. 1A is a sagittal view of an illustrative embodiment of a delivery instrument 100 designed to insert a LIF cage into an intervertebral space. FIG. 1B depicts the delivery instrument 100 and illustrates another view of the articulated joint 114 and the internal actuator rod 104. FIG. 1C is a detail of the articulated joint 114. FIG. 1A depicts a main body portion 102, and a sliding actuator portion or actuator portion 106 slidably coupled to the main body portion 102. An embodiment of a first actuator or actuator mechanism, such as a threaded knob 112 rotatably mounted on a proximal end of the delivery instrument 100, may couple the sliding actuator 106 to the main body portion 102. A second actuator, such as a handle 108, may be pivotally coupled to the main body portion 102 and, by way of a link member 110, the handle 108 may be further coupled to an internal actuator rod 104. At a distal end of the delivery instrument 100, an articulated joint 114 of certain embodiments may comprise a pair of grasping plates, or first and second grasping or fastening members, 118A and 118B, rotatably mounted on a pin 124. The distal ends of grasping plates 118 may be configured to support an intervertebral implant device, such as an LIF cage, one embodiment of which is shown here as an implant device 120, releaseably grasped by the grasping plates 118.

Figure 1D:
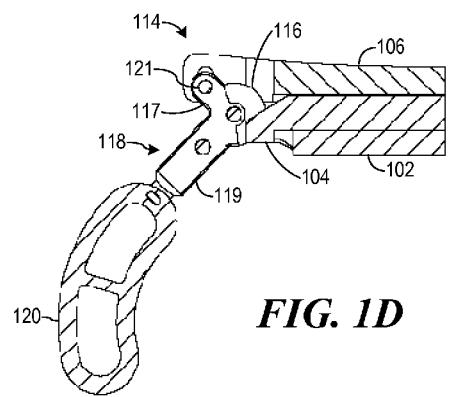
FIG. 1D is a sectional detail of the articulated joint shown in FIG. 1C.
Figure 3A:
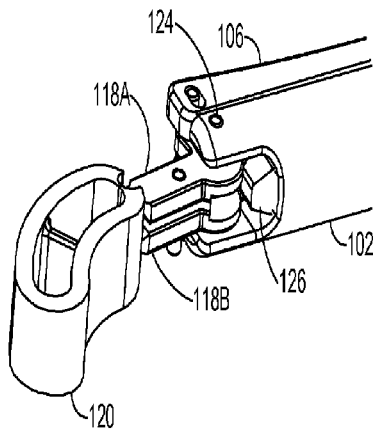
FIG. 3A-3D are perspective views illustrating operation of the articulated joint.
Figure 3B:
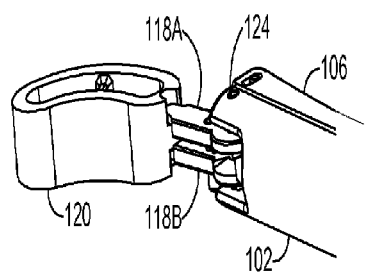
Figure 3C:
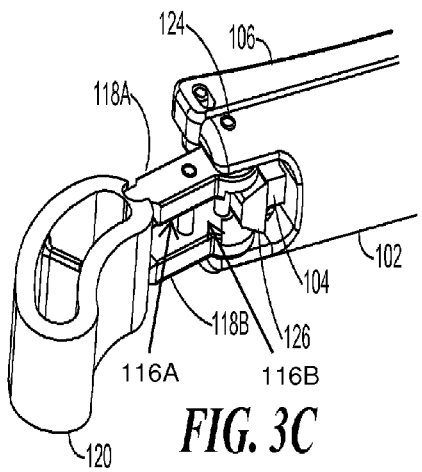
Figure 3D:
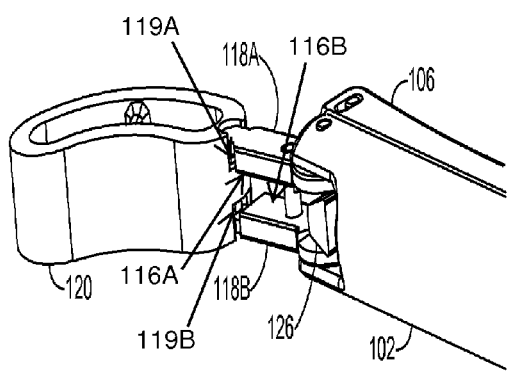

As shown in FIG. 1D, each of the grasping plates 118 may be configured to have a circular portion 116, a thumb portion 117, and an extended finger portion 119. Thumb portions 117 may be rotatably coupled to the proximal end of sliding actuator portion 106 by a pin 121. Extended finger portions 119 may rigidly and removably grasp the implant device 120. As shown in FIG. 3D, protrusions 119A and 119B of the extended finger portions 119 may be securely fitted within corresponding recesses located within the implant device 120. Therefore, when the implant device 120 is attached to an end of the delivery instrument 100, the implant device 120 may be restrained from translating or rotating relative to the extended finger portions 119. As shown in FIG. 1D, some illustrative embodiments of the extended finger portions 119 may comprise a rectangularly shaped protrusion, for example, for insertion within a similarly shaped slot located in an implant device 120. Further details of an embodiment of grasping plates 118 grasping the implant device 120 are depicted in FIGS. 3A-3D.

Figure 2A:
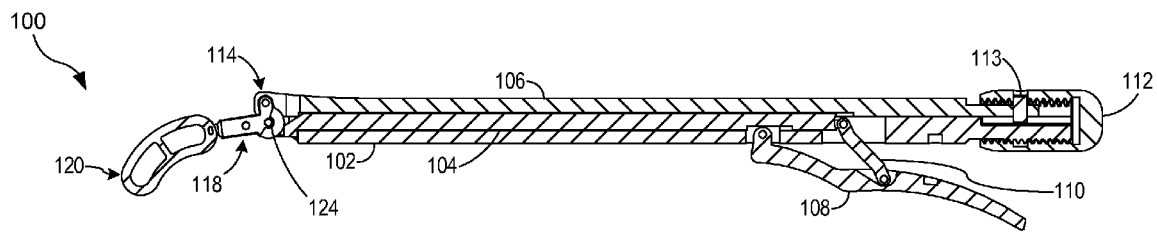
FIGS. 2A-2B are sectional views illustrating operation of the delivery instrument.
Figure 2B:
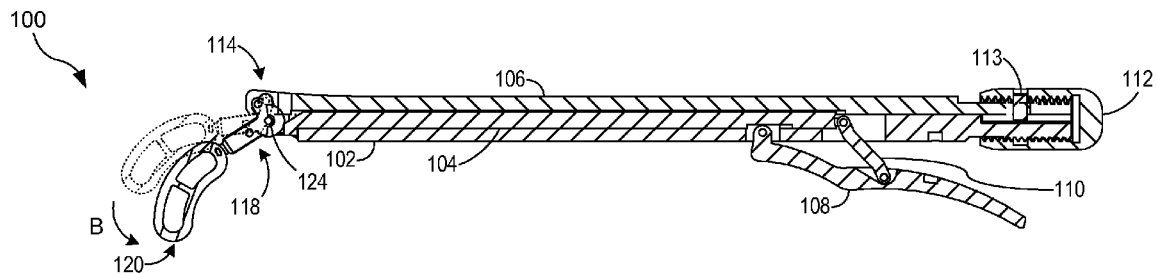

FIGS. 2A-2B are sectional views of an embodiment of the delivery instrument 100, illustrating an operation of an embodiment of the articulated joint 114. The threaded knob 112 may be rotatably mounted on a proximal end of the delivery instrument 100, coupling the main body portion 102 to the sliding actuator portion 106. In an illustrative embodiment of the threaded knob 112, internal threads may be formed within the knob 112 to mate with external threads formed on a proximal end of main body portion 102. A pin 113 disposed within the sliding actuator 106 may couple the knob 112 to the sliding actuator 106 via an internal groove located within the knob 112. As the knob 112 is rotated, the threaded coupling advances or retracts the sliding actuator 106 via the pin 113 moving through the groove. This may cause the articulated joint 114 to rotate about an axis through a pivot pin or central pivot 124, which axis is nominally perpendicular to a vertebral endplate. As the knob 112 is rotated in one direction, the threaded coupling between the knob 112 and the main body portion 102 may advance the sliding actuator 106 forward with respect to the main body 102. Advancement of the sliding actuator 106 may pivot the articulated joint 114 about an attachment point 124 and arcuately move the implant device 120 through an arc "B."

To release the implant device 120, a trigger 108 in certain embodiments may be pressed against the main body portion 102, thereby advancing an internal actuator rod 104 by way of a coupling established through link member 110, between the trigger 108 and the actuator rod 104. As shown in FIGS. 3C-3D, a wedge portion 126 formed at the distal end of the actuator rod 104 is thereby forced between the inner surfaces 116A and 116B of each of the grasping plates 118, forcing the grasping plates 118A and 118B apart. Grasping plate 118A is separated far enough from grasping plate 118B so that the protrusions at the ends of each finger 119 may be removed from their corresponding recesses in the implant device 120. At this point, the implant may be released from the implant device 120.

A surgeon may use the delivery instrument 100 to appropriately position and release the implant device within an intervertebral space in vivo. The surgeon may reset the instrument 100 to an initial configuration, comprising open grasping plates 118A and 118B and a relatively coincident articulated joint 114. The implant device 120 may be placed between the open grasping plates 118A and 118B and secured by moving the trigger 108 away from the main body portion 102, in some embodiments.

The implant device 120, secured to the delivery instrument 100, is then inserted in vivo. The surgeon may place the implant device 120 proximal to the intervertebral space. In some cases, the surgeon may have to strike the proximate end of the delivery instrument 100 in order to drive the implant device 120 into the intervertebral space. Once within the intervertebral space, the implant device 120 may be further positioned and rotated into an appropriate configuration.

Removing the delivery instrument 100 initially requires opening the grasping plates 118A and 118B by moving the trigger 108 closer to the main body portion 102, in some embodiments. The delivery instrument 100 may then be moved so as to clear the end of the implant device 120. Once clear, the articulated joint 114 may then be rotated to be relatively coincident with the main body portion 102. The delivery instrument 100 may then be removed from in vivo.

Having thus described the present invention by reference to certain of exemplary embodiments, it is noted that the embodiments disclosed are illustrative rather than limiting in nature and that a wide range of variations, modifications, changes, and substitutions are contemplated in the foregoing disclosure. In some instances, some features of an embodiment of the present invention may be employed without a corresponding use of the other features. Many such variations and modifications may be considered desirable by those skilled in the art based upon a review of the foregoing description of illustrative embodiments. Accordingly, it is appropriate that the appended claims be construed broadly and in a manner consistent with the scope of the invention.

What is claimed is:
1. An instrument comprising:
a body portion having a first distal end and a first proximal end coupled by a first longitudinal axis;
an actuator portion having a second distal end and a second proximal end coupled by a second longitudinal axis that is substantially parallel to said first longitudinal axis;
a threaded rotational member threadingly engaged to a threaded portion of one of said first and second proximal ends, wherein a longitudinal position of said threaded rotational member relative to said body and actuator portions is fixed with respect to another one of said body and actuator portions;
rotatable first and second fastening members movably coupled to said body and actuator portions, wherein said first and second fastening members are rotatable from a first position to a second position around a pivot axis that is substantially perpendicular to said first longitudinal axis, wherein said first and second fastening members are separated by a space designed to receive a portion of an interbody insert therein;
said first and second fastening members are movably coupled to said body and actuator portions to enable a distance along said pivot axis between said first and second fastening members to be varied;

an actuator rod having a third distal end and a third proximal end coupled by a third longitudinal axis that is substantially parallel to said first longitudinal axis; and
a trigger pivotally coupled to said body portion and said actuator rod.

2. The instrument of claim 1 wherein said actuator rod is positioned between said body portion and said actuator portion.

3. The instrument of claim 1 wherein said first fastening member includes a first inner surface facing a second inner surface of said second fastening member, and wherein said first and second fastening members are movably coupled to said body and actuator portions to enable said distance along said pivot axis between said first and second inner surfaces to be varied.

4. The instrument of claim 3 wherein said third distal end includes a wedge sized to enter said space between said first and second inner surfaces to vary said distance between said first and second inner surfaces when said third distal end is moved relative to said first distal end.

5. The instrument of claim 1 wherein said threaded rotational member is fixed with respect to said one of said body and actuator portions by a pin positioned substantially perpendicularly to said first or second longitudinal axis, respectively.

6. An instrument for delivering an insert, said instrument comprising:
a body;
a sliding actuator translatingly coupled to said body;
a rotating member pivotally connected to a distal end of said body and said sliding actuator and configured to releasably retain an insert, wherein said rotating member includes a first grasping member and a second grasping member, wherein said first grasping member and said second grasping member are configured to translate relative to one another along a central axis of said pivotal connection to one of said body and said sliding actuator;
a first actuator having a threaded member operatively coupled to said body and said sliding actuator, wherein rotation of said threaded member translates said sliding actuator with respect to said body, and wherein translation of said sliding actuator with respect to said body rotates said rotating member about said pivotal connections; and
a second actuator operatively coupled to said rotating member and configured to transition said rotating member between release and retention of the insert.

7. The instrument of claim 6
wherein said second actuator operates to translate said first grasping member relative to said second grasping member between a first position and a second position; and
wherein a first distance between said first grasping member and said second grasping member in said first position is greater than a second distance between said first grasping member and said second grasping member in said second position.

8. The instrument of claim 7 wherein
said second actuator further comprises a wedging member; and
wherein operating said second actuator slidingly interfaces said wedging member with said rotating member such that said first grasping member and said second grasping member are translated between said first position and said second position.

9. The instrument of claim 7 wherein said first grasping member and said second grasping member each comprise a protrusion configured to releasably retain the insert.

10. The instrument of claim 6 wherein said threaded member comprises a knob positioned at a proximal end of said body and said sliding actuator.

11. A delivery instrument for an insert, said instrument comprising:
a body;
a sliding actuator slidably engaged with said body;
a threaded first actuator rotatably interacting with said body and said sliding actuator such that rotation of said first actuator translates said sliding actuator relative to said body;
a first grasping member and a second grasping member that each comprise a first protrusion, a second protrusion, and a central pivot, wherein each of said first grasping member and said second grasping member rotates in a plane of rotation about said central pivots;
a second actuator configured to interact with said first grasping member and said second grasping member such that operation of said second actuator causes said first grasping member and said second grasping member to approach and withdraw from one another in a direction transverse to said plane of rotation;
wherein said first protrusions are configured to engage the insert;
wherein said central pivots are pivotally connected to said body;
wherein said second protrusions are pivotally connected to said sliding actuator; and
wherein translation of said sliding actuator translating relative to said body rotates said first grasping member and said second grasping member about said central pivots in said plane of rotation.

12. The instrument of claim 11 wherein said first actuator comprises a knob threadably engaged with a proximal end of said body;
wherein said knob is slidingly coupled to said sliding actuator via a pin attached to said sliding actuator and a groove within said knob; and
wherein rotating said knob translates said sliding actuator relative to said body.

13. The instrument of claim 11 wherein said second actuator comprises a wedging member slidingly interacting with said first grasping member and said second grasping member; and wherein operating said second actuator inserts and withdraws said wedging member between said first grasping member and said second grasping member.

14. The instrument of claim 13 wherein said second actuator further comprises a link and a handle member;
wherein said handle member is pivotally connected to said body;
wherein said wedging member is pivotally coupled to said handle via said link; and
wherein operating said handle member translates said wedging member relative to said first grasping member and said second grasping member.

* * * * *